United States Patent [19]

Andrade et al.

[11] Patent Number: 4,675,451

[45] Date of Patent: Jun. 23, 1987

[54] PROCESS FOR THE PREPARATION OF 2-ALKYL-1,4-BUTANEDIAL

[75] Inventors: Juan Andrade, Kleinostheim; Guenter Prescher, Hanau, both of Fed. Rep. of Germany; Marc Samson, Lokeren, Belgium

[73] Assignee: Degussa Aktiengesellschaft, Frankfurt, Fed. Rep. of Germany

[21] Appl. No.: 828,488

[22] Filed: Feb. 12, 1986

[30] Foreign Application Priority Data

Feb. 19, 1985 [DE] Fed. Rep. of Germany ....... 3505654

[51] Int. Cl.$^4$ .............................................. C07C 45/49
[52] U.S. Cl. .................................... 568/486; 568/454
[58] Field of Search ................................. 568/486, 454

[56] References Cited

U.S. PATENT DOCUMENTS

| | | | |
|---|---|---|---|
| 3,189,655 | 6/1965 | Thompson | 568/486 |
| 3,527,809 | 9/1970 | Pruett et al. | 568/454 |
| 3,928,459 | 12/1975 | Mercier | 568/486 |
| 4,467,120 | 9/1984 | Fischer et al. | 568/485 |
| 4,507,508 | 3/1985 | Hayden et al. | 568/486 |

*Primary Examiner*—Werren B. Lone
*Attorney, Agent, or Firm*—Beveridge, DeGrandi & Weilacher

[57] ABSTRACT

A process is disclosed for the preparation of 2-alkyl-1,4-butanedial by hydroformylation of acetals of a 2-alkyl-substituted-1-propenal in the presence of a complex rhodium catalyst. The 3-alkyl-4,4-dialkoxybutanal obtained in this manner is separated and hydrolyzed to the desired compound.

15 Claims, No Drawings

PROCESS FOR THE PREPARATION OF 2-ALKYL-1,4-BUTANEDIAL

The invention relates to a process for the preparation of 2-alkyl-1,4-butanedial.

The preparation of 3-alkyl-4,4-dialkoxybutanol by hydroformylation of alpha, beta-unsaturated aldehyde acetals in the presence of a catalyst having the formula RhCl(Co)(PPh$_3$)$_2$ is known in the art.

The reaction is carried out in benzene as a solvent and in the presence of triethylamine, which is presumed to be helpful in avoiding side reactions (C. Botteghi et al., J. Org. Chem, 58 (1973), 2361–2365; Chim, Ind. (Milan) 52 (1970), 265).

According to German patent application No. 1793069 ≙ U.S Pat. No. 3,527,908) other triarylphosphine/rhodium/carbonyl complex catalysts are likewise suitable for catalyzing the hydroformylation of alpha-olefin compounds to aldehydes. According to this process, however, one must also accept the formation of mixtures of n- and isoaldehydes. Under otherwise identical conditions, the employment of a solvent results in a reduction of the n-aldehyde portion. The dialdehydes produced in the manner taught by the said document are suitable as hardener components in developer solutions (Research Disclosure, Apr. 1981, 149).

It is an object of the invention to provide a process for the preparation of 2-alkyl-1,4-butanedial, which produces homogeneous products without employment of triethylamine and solvents.

According to a feature of the invention, there is provided a process for the preparation of 2-alkyl-1,4-butanedial, in which the acetal of a 2-alkyl-substituted 1-propenal (2-alkyl-3,3-dialkoxy-1-propene) is hydroformylated in the presence of a complex catalyst containing rhodium and trivalent organic phosphorus compounds as ligands, wherein (1) hydridotris(triphenylphosphine)rhodium carbonyl together with triphenylphosphine and/or triphenylphosphite is used as the catalyst, (2) the 3-alkyl-4,4-dialkoxybutanal is separated from the hydroformylation product, and (3) the product obtained thereby is hydrolyzed to 2-alkyl-1,4-butanedial.

The components of the catalyst system used in accordance with the invention; i.e. the hydridotris-(triphenylphosphine)rhodium carbonyl, triphenylphosphine and triphenylphosphite are individually known chemical compounds and available in the art.

This process gives the desired product in high yields without use of solvents and triethylamine, without reduction in yield by isomer formation.

To carry out the process according to the invention, the 2-alkyl-1-propenal is first reacted with an alkanol to form a 2-alkyl-3,3-dialkoxy-1-propene. Preferably, a 2-alkyl-3,3-dialkoxy-1-propene is selected which has 1 to 6 carbon atoms in each alkoxy group. Particularly suitable are 2-alkyl-3,3-dimethoxy-1-propene and 2-alkyl-3,3-diethoxy-1-propene. The process is carried out in a manner known from the prior art, for example, in accordance with the process described in Org. Synth, Coll. Vol. 4 (1963), pages 21 to 22, by reaction of the orthoformic acid ester of the corresponding alkanols with acrolein or according to the process disclosed in West German Pat. No. 930,752 or in U.S. Pat. No. 2,626,283 by reaction of the corresponding alkanols with the aldehyde in the presence of strong acids as catalysts.

The process disclosed in West German patent application No. 3403426 is used advantageously in the preparation of 2-alkyl-3,3-dimethoxy-1-propene and 2-alkyl-3, 3-diethoxy-1-propene. The alkyl group substitu at position 2 has 1 to 4 carbon atoms and is branched or straight-chained. Methyl, ethyl, n-propyl, isopropyl, n-butyl, and isobutyl groups are preferred.

To continue the process embodying the invention, the 2-alkyl-3,3-dialkoxy-1-propene is hydroformylated by reaction with a gas mixture of hydrogen and carbon monoxide in the presence of the catalyst. Advantageously, the reaction occurs at a high temperature, preferably at temperatures of from 100° to 140° C. The pressure can in many cases be largely selected as desired, but it is generally expedient to work at least at normal atmospheric pressure. Pressures of from 1 to 60 bar are preferred. Advantageously, at least stoichiometric amounts, preferably excess amounts, of hydrogen and carbon monoxide are employed, whereby the molar ratio of hydrogen to carbon monoxide can in many cases be selected as desired, but is preferably from 0.5–1.0 to 1.0–0.5.

For the hydroformylation, hydridotris(triphenylphosphine)rhodium carbonyl mixed with triphenylphosphine and triphenylphosphite is used as the catalyst. It is also within the scope of the invention to employ triphenylphosphite together with the rhodium carbonyl compound, without triphenylphosphine. Likewise, the rhodium carbonyl compound may be used together with triphenylphosphine as the catalyst. Such catalysts are described in West German patent application No. 1793069. Preferably, when carrying out the process incorporating the invention, approximately 0.0001 to 0.0070 parts by weight of the hydridotris(triphenylphosphine)rhodium carbonyl and 0.00–0.06 parts by weight of the triphenylphosphine or triphenylphosphite, or both, are used per part by weight of the 2-alkyl-3,3-dialkoxy-1-propene.

The hydroformylation product is fractionated to recover the 3-alkyl-4,4-dialkoxybutanal. In this case, the process is carried out advantageously at reduced pressure, preferably at pressures below 40 mbar.

The 3-alkyl-4,4-dialkoxybutanal thus recovered is finally converted to 2-alkyl-1,4-butanedial by hydrolysis. The hydrolysis is performed in an acidic, preferably highly acidic, medium, with particular advantage in the presence of an acidic ion exchanger, advantageously at temperatures below 30° C., preferably between 5° and 15° C. Acidic ion exchange resins are widely known and available for this purpose.

The following examples serve to illustrate the claimed invention and are not intended to be limiting thereof.

EXAMPLE 1

2-methyl-3,3-dimethoxy-1-propene (263 g) was placed in an agitated autoclave with 2.6 g of triphenylphosphite and 0.4 g of hydridotris(triphenylphosphine) rhodium carbonyl. Then a mixture of equal parts by volume of hydrogen and carbon monoxide was charged into the autoclave at a pressure of 6 bar. The temperature in the autoclave was maintained at 115° C. in the process. Gas was no longer taken up after 150 min and the charging ended. The gas chromatographic analysis revealed that 99% of 2-methyl-3, 3-dimethoxy-1-propene had reacted. The reaction mixture containing 94%

3-methyl-4,4-dimethoxybutanal was distilled at 20 mbar. The desired 3-methyl-4,4-dimethoxybutanal was recovered at 75° C. It was dissolved in equal parts by volume of water; the solution was combined with 60 g of the ion exchange resin DOWEX MSC-1*; the mixture was agitated for 2 hours at 20° C., then filtered. A 32% aqueous solution of 2-methyl-1,4-butanedial was obtained as the filtrate. The yield of 1,4-butanedial relative to the starting 2-methyl-3(3-dimethoxy-1-propene was 94%.

*An acidic ion exchange resin that is commercially available. Any suitable commercially available acidic ion exchange resin may be used for this purpose.

EXAMPLE 2

The process was carried out as in Example 1, but 232 g (2.0 mol) of 2-methyl-3,3-dimethoxy-1-propene was added with 0.71 g of triphenylphosphite and 0.3 g of hydridotris(triphenylphosphine)rhodium carbonyl, and hydroformylation occurred at 30 bar and 130° C. It was found that 99.8% of the 2-methyl-3,3-dimethoxy-1-propene had reacted. The reaction mixture contained 97.4% 3-methyl-4,4-dimethoxybutanal. The yield of 2-methyl-1,4-butanedial relative to the starting 2-methyl-3,3-dimethoxy-1-propene was 97%.

EXAMPLE 3

The process was carried out as in Example 1, but 350 g (about 3.0 mol) of 2-methyl-3,3-dimethoxy-1-propene was added with 6.0 g of triphenylphosphite and 0.7 g of hydridotris(triphenylphosphine)rhodium carbonyl, and hydroformylation occurred at 50 bar and 105° C. 99.9% of 2-methyl-3,3-dimethoxy-1-propene had reacted. The reaction mixture contained 98% 3-methyl-4,4-dimethoxybutanal. The yield of 2-methyl-1,4-butanedial relative to the starting 2-methyl-3,3-dimethoxy-1-propene was 97%.

EXAMPLE 4

The process was carried out as in Example 1, but 200.0 g (1.41 mol) of 2-ethyl-3,3-dimethoxy-1-propene was added with 1.0 g of triphenylphosphite and 0.6 g of hydridotris(triphenylphosphine)rhodium carbonyl, and the hydroformylation was carried out at 8 bar and 119° C.; gas uptake ended after 160 minutes. It was found that 81% of the 2-ethyl-3,3-dimethoxy-1-propene had reacted. The reaction mixture was distilled in vacuum. The desired 3-ethyl-4,4-dimethoxybutanal was converted at 85° C. and 20 mbar. The product, 2-ethyl-1,4-butanedial, was then recovered following the same steps as in Example 1.

EXAMPLE 5

The process was carried out as in Example 1, but 200 g (1.39 mol) of 2-n-propyl-3,3-dimethoxy-1-propene was added with 1.3 g of triphenylphosphite and 0.5 g of hydridotris(triphenylphosphine)rhodium carbonyl, and the hydroformylation was conducted at 6 bar and 127° C.; gas uptake ended after 180 minutes. It was determined that 85% of the 2-n-propyl-3,3-dimethoxy-1-propene had reacted. The reaction mixture was distilled in vacuum. The desired 3-n-propyl-4,4-dimethoxybutanal was converted at 100 to 102° C and 20 mbar. The product, 2-n-propyl-1,4-butanedial, was then recovered as in Example 1.

EXAMPLE 6

Following the procedure as described in Example 1, 200 g (1.39 mol) of 2-iso-propyl-3,3-dimethoxy-1-propene was charged to the autoclave. After 300 minutes, it was found that 50% of the 2-isopropyl-3,3-dimethoxy-1-propene had reacted. The desired 3-isopropyl-4,4-dimethoxybutanal was recovered at 94° to 96° C. and 20 mbar. The product, 2-iso-propyl-1,4-butanedial, was then recovered as in Example 1.

EXAMPLE 7

Utilizing essentially the same reactants and conditions as in Example 1, a combination of hydridotris-(triphenylphosphine)rhodium carbonyl, triphenylphosphine and triphenylphosphite can be used as the catalyst to produce the corresponding product.

EXAMPLE 8

In like manner according to the procedure set forth in Example 1, a combination of hydridotris(tri-phenylphosphine)rhodium carbonyl and triphenylphosphine can be used as the catalyst to produce the corresponding product.

Further variations and modifications of the foregoing invention will be apparent to those skilled in the art from a consideration of the above. Such modifications and variations are intended to be encompassed by the claims appended hereto.

The German priority application No. P 35 05 654.1 is relied on and incorporated herein by reference.

We claim:

1. A process for the preparation of 2-alkyl-1,4-butanedial comprising hydroformylating the acetal of a 2-alkyl-substituted-1-propenol by reaction with a gas mixture of hydrogen and carbon monoxide at elevated temperature and at least normal atmospheric pressure in the presence of a complex catalyst containing rhodium and trivalent organic phosphorus compounds as ligands, and in the absence of solvents wherein hydridotris(triphenylophosphine) rhodium carbonyl together with triphenylphosphine and/or triphenylphosphite is used as the catalyst, to thereby obtain a 3-alkyl-4,4-dialkoxybutanal, in a hydroformylation product, separating the 3-alkyl-4,4-dialkoxybutanal from the hydroformylation product and hydrolyzing the 3-alkyl-4,4-dialkoxybutanal to 2-alkyl-1,4-butanedial.

2. The process according to claim 1 wherein a 2-alkyl-1-propenal is initially reacted with an alkanol to form a 2-alkyl-3,3-dialkoxy-1-propene.

3. The process according to claim 2, wherein the alkanol contains 1 to 6 carbon atoms.

4. The process according to claim 1, wherein 2-alkyl-3,3-dimethoxy-1-propene is used.

5. The process according to claim 1, wherein 2-alkyl-3,3-diethoxy-1-propene is used.

6. The process according to claim 1, wherein a 3,3-dialkoxy-1-propene is employed which is substituted at position 2 with a straight-chain or branch-chain $C_1$–$C_4$ alkyl.

7. The process according to claim 1, wherein the 0.0001–0.0070 parts by weight of hydriotris(triphenylphosphine)rhodium carbonyl, 0.001-0.06 parts by weight of the triphenylphosphine or triphenylphosphite is used per part of propene.

8. The process according to claim 1, wherein the hydroformylation is carried out at temperature of from 100° to 140° C. and pressures of from 1 to 60 bar.

9. The process according to claim 1, wherein the hydroformylation is carried out using a gas mixture of hydrogen and carbon monoxide.

10. The process according to claim 9, wherein the molar ratio of hydrogen to carbon monoxide is 0.5–1.0 to 1.0 to 0.5.

11. The process according to claim 1, wherein the hydroformylation product is fractionated to recover the 3-alkyl-4,4-dialkoxybutanal.

12. The process according to claim 11, wherein the process is carried out at pressures below 40 mbar.

13. The process according to claim 1, wherein the 3-alkyl-4,4-dialkoxybutanal is hydrolyzed in an acidic medium.

14. The process according to claim 13, wherein an acidic ion exchange resin is used.

15. The process according to claim 14, wherein the temperature is below 30° C.

* * * * *